(12) United States Patent
Morita

(10) Patent No.: US 12,053,162 B2
(45) Date of Patent: Aug. 6, 2024

(54) DISTAL END PORTION OF AN ENDOSCOPE HAVING ELECTRONIC COMPONENTS AND CORRESPONDING SPACES FOR WIRING AND ENDOSCOPE HAVING THE DISTAL END PORTION

(71) Applicant: OLYMPUS CORPORATION, Tokyo (JP)

(72) Inventor: Mitsuhiko Morita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 556 days.

(21) Appl. No.: 17/342,909

(22) Filed: Jun. 9, 2021

(65) Prior Publication Data

US 2021/0290041 A1 Sep. 23, 2021

Related U.S. Application Data

(63) Continuation of application No. PCT/JP2018/045675, filed on Dec. 12, 2018.

(51) Int. Cl.
*A61B 1/06* (2006.01)
*A61B 1/00* (2006.01)
(Continued)

(52) U.S. Cl.
CPC ........ *A61B 1/0684* (2013.01); *A61B 1/00087* (2013.01); *A61B 1/00114* (2013.01);
(Continued)

(58) Field of Classification Search
None
See application file for complete search history.

(56) References Cited

U.S. PATENT DOCUMENTS 5,257,617 A 11/1993 Takahashi
5,329,935 A 7/1994 Takahashi
(Continued)

FOREIGN PATENT DOCUMENTS

CA 2 647 076 A1 9/2008
EP 2 674 095 A1 12/2013
(Continued)

OTHER PUBLICATIONS

International Search Report dated Mar. 12, 2019 received in PCT/JP2018/045675.

*Primary Examiner* — John P Leubecker
(74) *Attorney, Agent, or Firm* — Scully, Scott, Murphy & Presser, P.C.

(57) ABSTRACT

A distal end portion of an endoscope includes: a distal end cover disposed at a distal end of an insertion portion; a distal end member configured to be inserted into and fitted to the distal end cover, the distal end member including a first side surface and a second side surface, the first side surface being configured to come into surface contact with an inner surface of the distal end cover, the second side surface being formed in a radially inward direction with respect to the first side surface, the second side surface forming a space by being separated from the inner surface of the distal end cover by a predetermined distance; an electronic component mounted on a distal end surface of the distal end member; and a wiring electrically connected to the electronic component and disposed in a space formed between the inner surface of the distal end cover and the second side surface of the distal end member.

18 Claims, 10 Drawing Sheets

(51) Int. Cl.
*A61B 1/005* (2006.01)
*A61B 1/05* (2006.01)

(52) U.S. Cl.
CPC ........ *A61B 1/00147* (2013.01); *A61B 1/0051* (2013.01); *A61B 1/05* (2013.01); *A61B 1/005* (2013.01)

(56) References Cited

U.S. PATENT DOCUMENTS

| | | |
|---|---|---|
| 6,447,445 B1 | 9/2002 | Hirano |
| 2003/0222325 A1* | 12/2003 | Jacobsen .................. A61B 1/05 257/434 |
| 2006/0058584 A1* | 3/2006 | Hirata .................. A61B 1/0684 600/179 |
| 2006/0146172 A1* | 7/2006 | Jacobsen ................ H04N 23/50 348/340 |
| 2007/0173695 A1* | 7/2007 | Hirata ................ G02B 23/2461 600/152 |
| 2007/0249907 A1 | 10/2007 | Boulais et al. |
| 2008/0055403 A1* | 3/2008 | Salman .................... A61B 1/05 348/76 |
| 2008/0255416 A1* | 10/2008 | Gilboa .................. A61B 1/055 600/110 |
| 2011/0295072 A1* | 12/2011 | Boulais .............. A61B 1/00096 600/176 |
| 2013/0303853 A1 | 11/2013 | Takahashi et al. |
| 2016/0345806 A1* | 12/2016 | Ishii .................... A61B 1/00128 |
| 2017/0127915 A1* | 5/2017 | Viebach ................ A61B 1/018 |
| 2017/0238903 A1* | 8/2017 | Wood ................ A61B 17/3478 |
| 2020/0316349 A1* | 10/2020 | Smith ...................... A61B 1/01 |

FOREIGN PATENT DOCUMENTS

| | | |
|---|---|---|
| JP | 10-118014 A | 5/1998 |
| JP | 2802952 B2 | 9/1998 |
| JP | 2001-083436 A | 3/2001 |
| JP | 2006-136671 A | 6/2006 |
| JP | 2009-534113 A | 9/2009 |
| JP | 2017-209278 A | 11/2017 |
| WO | 2007/124211 A2 | 11/2007 |
| WO | 2013/084548 A1 | 6/2013 |
| WO | 20151/22487 A1 | 8/2015 |

* cited by examiner

DISTAL END PORTION OF AN ENDOSCOPE HAVING ELECTRONIC COMPONENTS AND CORRESPONDING SPACES FOR WIRING AND ENDOSCOPE HAVING THE DISTAL END PORTION

CROSS-REFERENCE TO RELATED APPLICATION

This application is a continuation application of PCT/JP2018/045675 filed on Dec. 12, 2018, the entire contents of which are incorporated herein by this reference.

BACKGROUND OF THE INVENTION

1. Field of the Invention

The present invention relates to a distal end portion of an endoscope, which is provided at a distal end part of an insertion portion of the endoscope and in which electronic components are mounted.

2. Description of the Related Art

Conventionally, an endoscope has an insertion portion formed in an elongated tubular shape in accordance with an observation object and configured to be inserted into a lumen. A configuration of such an endoscope is known, in which electronic components such as an image pickup unit including a CCD or a CMOS, an illumination apparatus including an LED element, and the like are mounted in a distal end part of the insertion portion of the endoscope.

Such a configuration of the endoscope is disclosed in Japanese Patent Application Laid-Open Publication No. 2006-136671, for example. The Japanese Patent Application Laid-Open Publication No. 2006-136671 discloses a technology of an electronic endoscope. With the technology of the electronic endoscope, assemblability is improved without decreasing the optical performance, by preventing an image pickup unit from moving backward with respect to the distal end constituting portion when the image pickup unit is fixed with screws, while securing the mechanical fixing structure of lenses and following the screw fixing structure of the image pickup unit, even if a clearance exists at an assembling part between the image pickup unit and the distal end constituting portion.

SUMMARY OF THE INVENTION

A distal end portion of an endoscope according to one aspect of the present invention includes: a distal end cover disposed at a distal end of an insertion portion; a distal end member configured to be inserted into and fitted to the distal end cover, the distal end member including a first side surface and a second side surface, the first side surface being configured to come into surface contact with an inner surface of the distal end cover, the second side surface being formed in a radially inward direction with respect to the first side surface, the second side surface forming a space by being separated from the inner surface of the distal end cover by a predetermined distance; an electronic component mounted on a distal end surface of the distal end member, the electronic component having an outer shape formed in rectangle and being disposed such that one side of the rectangle is along the second side surface; and a wiring electrically connected to the electronic component from a side of the one side of the rectangle, the wiring being disposed in the space formed between the inner surface of the distal end cover and the second side surface of the distal end member.

An endoscope according to one aspect of the present invention includes: a distal end portion including: a distal end cover disposed at a distal end of an insertion portion; a distal end member configured to be inserted into and fitted to the distal end cover, the distal end member including a first side surface and a second side surface, the first side surface being configured to come into surface contact with an inner surface of the distal end cover, the second side surface being formed in a radially inward direction with respect to the first side surface, the second side surface forming a space by being separated from the inner surface of the distal end cover by a predetermined distance; an electronic component mounted on a distal end surface of the distal end member, the electronic component having an outer shape formed in rectangle and being disposed such that one side of the rectangle is along the second side surface; and a wiring electrically connected to the electronic component from a side of the one side of the rectangle, the wiring being disposed in the space formed between the inner surface of the distal end cover and the second side surface of the distal end member.

DETAILED DESCRIPTION OF THE PREFERRED EMBODIMENT(S)

Figure 1:
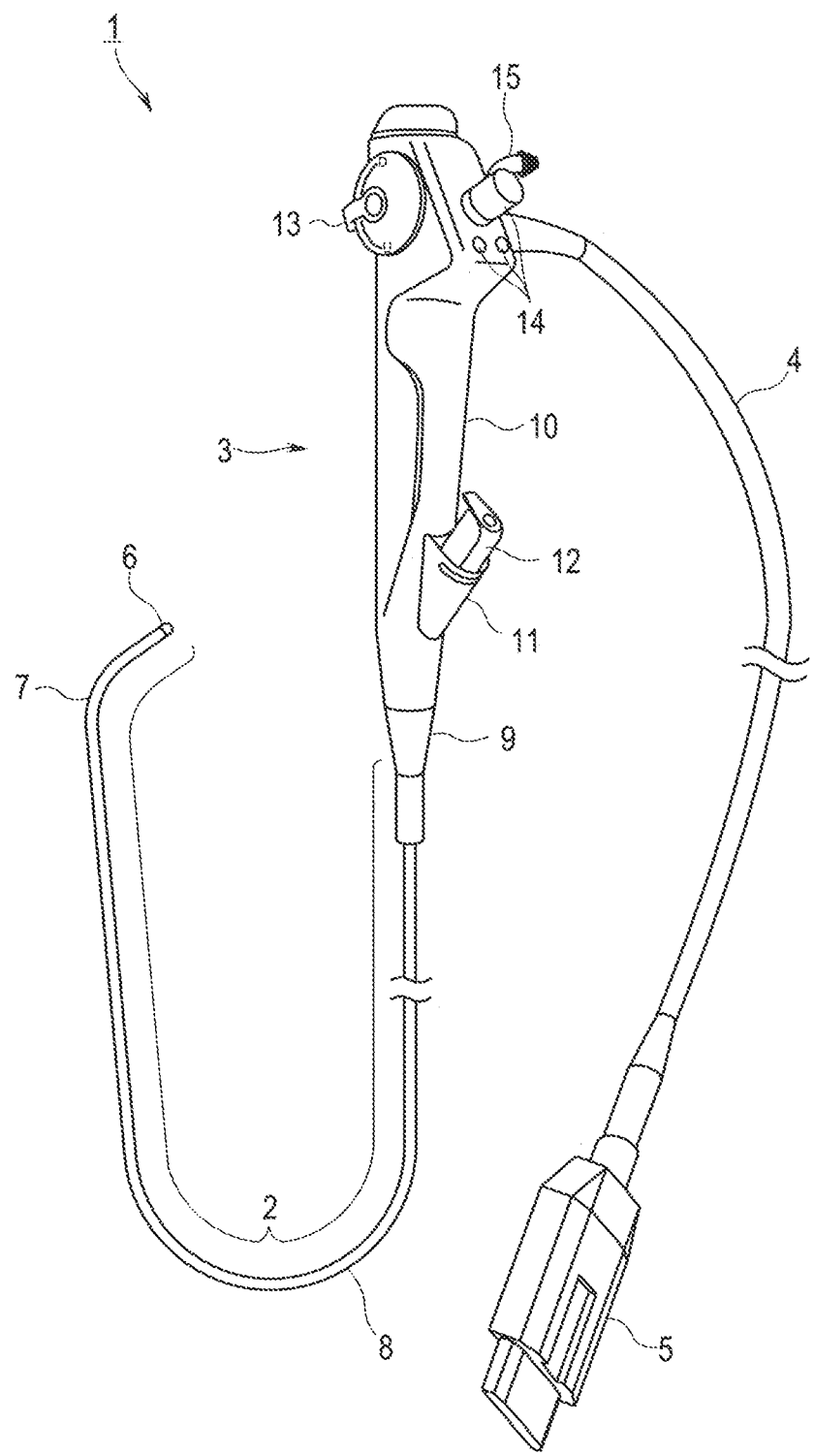
FIG. 1 is a perspective view illustrating a configuration of an endoscope according to an aspect of the present invention.

Hereinafter, a preferred embodiment of the present invention is described with reference to drawings. Note that a different scale size is used for each of the constituent elements in the drawings to be used for the description below in order to allow each of the constituent elements to be illustrated in a recognizable size in each of the drawings, and the present invention is not limited to the number, shapes, ratio of a size of a certain constituent element to sizes of other constituent elements, and a relative positional relationship among the constituent elements shown in these drawings. In addition, in the description below, there is a case where the up and down directions viewing toward the paper surface of the drawings are referred to as the upper portion and the lower portion of the constituent elements.

First, one aspect of the present invention will be described with reference to the drawings.

Hereinafter, description will be made on a schematic configuration of an endoscope including a distal end portion of an endoscope according to the present invention, with reference to the drawings.

Figure 2:
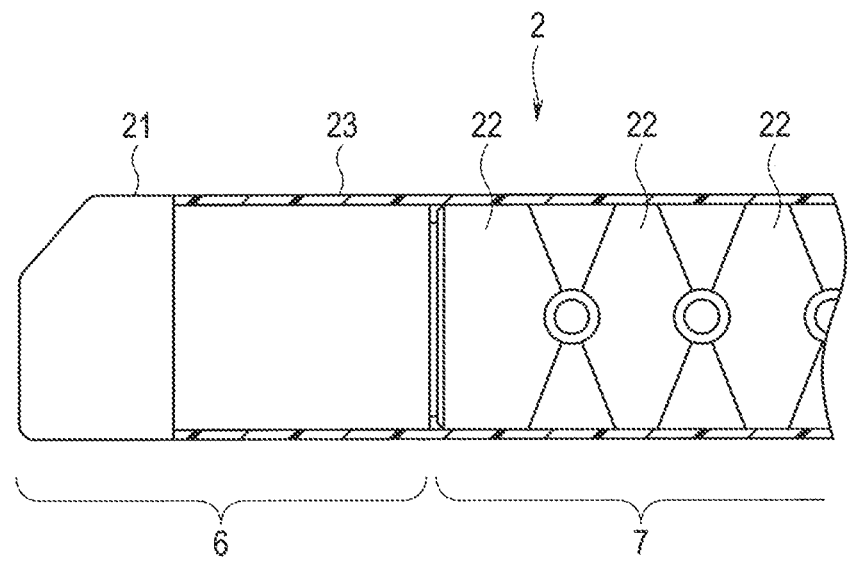
FIG. 2 is a cross-sectional view illustrating a configuration of a distal end part of an insertion portion of the endoscope according to the aspect of the present invention.
Figure 3:
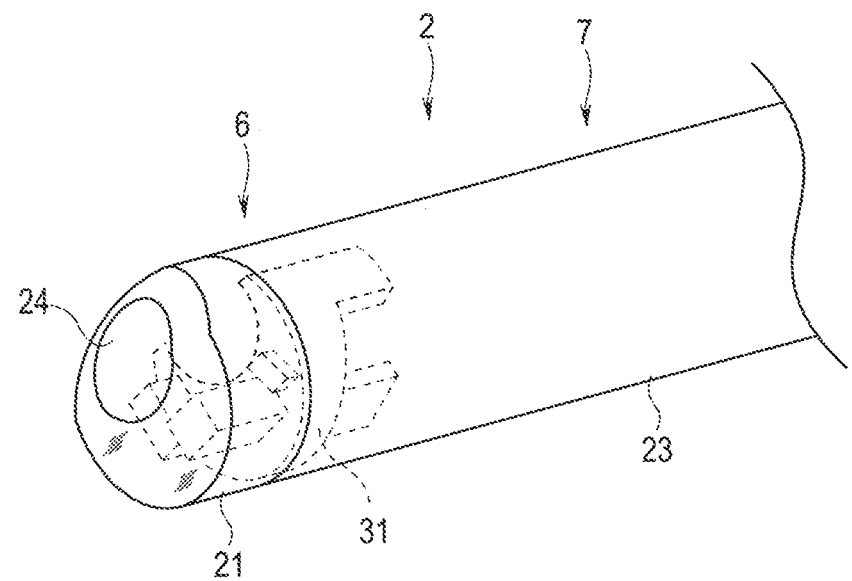
FIG. 3 is a perspective view illustrating the configuration of the distal end part of the insertion portion of the endoscope according to the aspect of the present invention.
Figure 4:
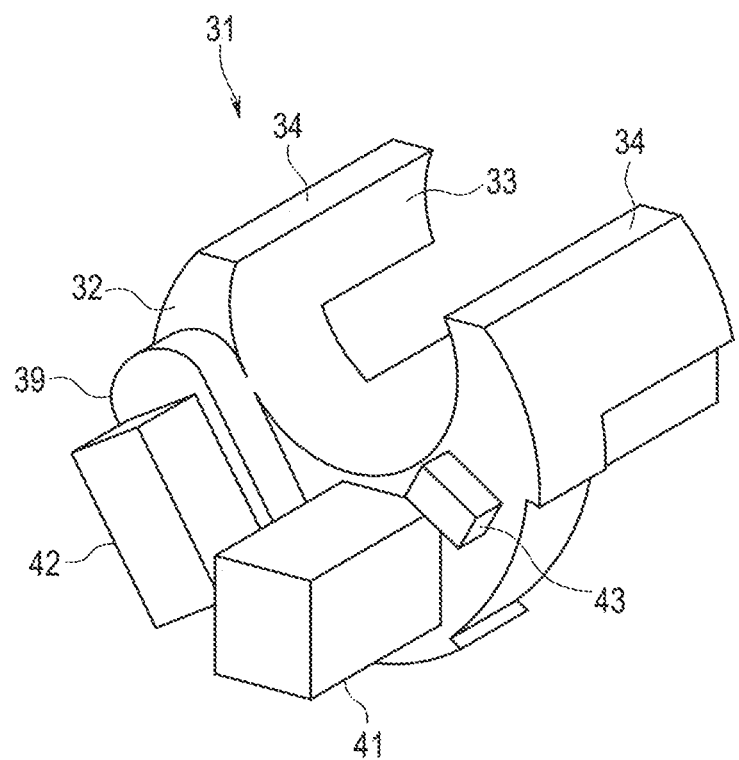
FIG. 4 is a perspective view illustrating a configuration of a distal end constituting portion of the endoscope according to the aspect of the present invention.
Figure 5:
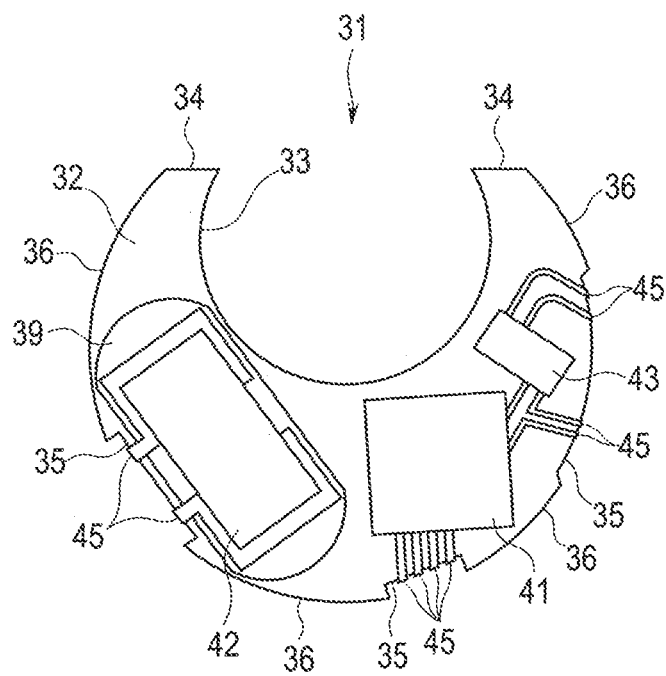
FIG. 5 is a front view illustrating the configuration of the distal end constituting portion of the endoscope according to the aspect of the present invention.
Figure 6:
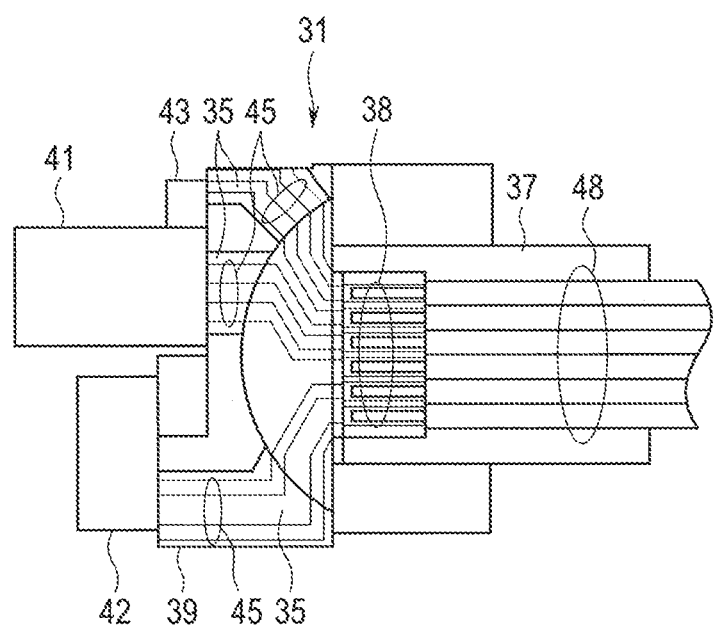
FIG. 6 is a plan view illustrating the configuration of the distal end constituting portion of the endoscope according to the aspect of the present invention, and showing a state where a plurality of cables are connected to the distal end constituting portion.
Figure 7:
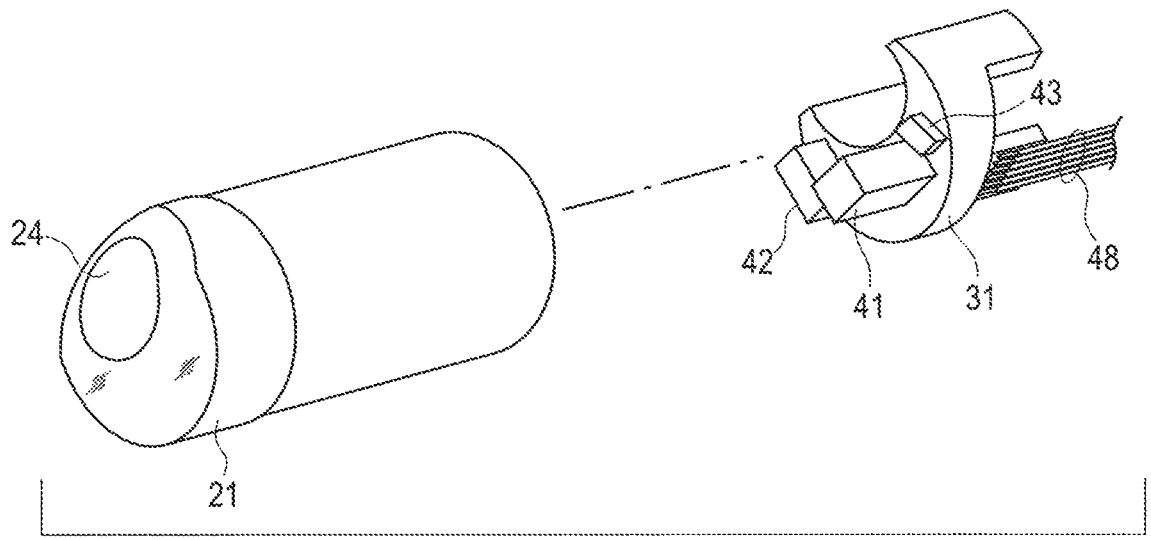
FIG. 7 is an exploded perspective view illustrating a distal end cover and the distal end constituting portion of the endoscope according to the aspect of the present invention.
Figure 8:
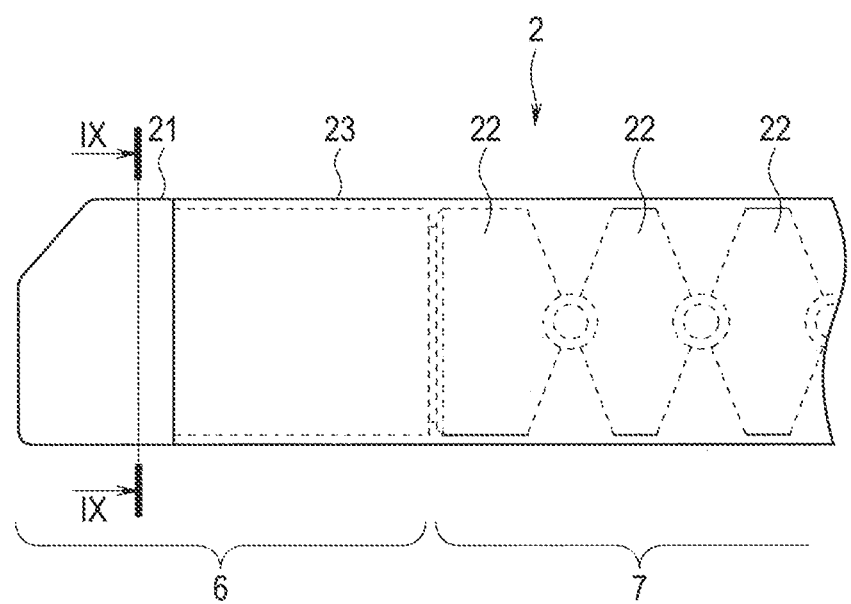
FIG. 8 is a side view illustrating the configuration of the distal end part of the insertion portion of the endoscope according to the aspect of the present invention.
Figure 9:
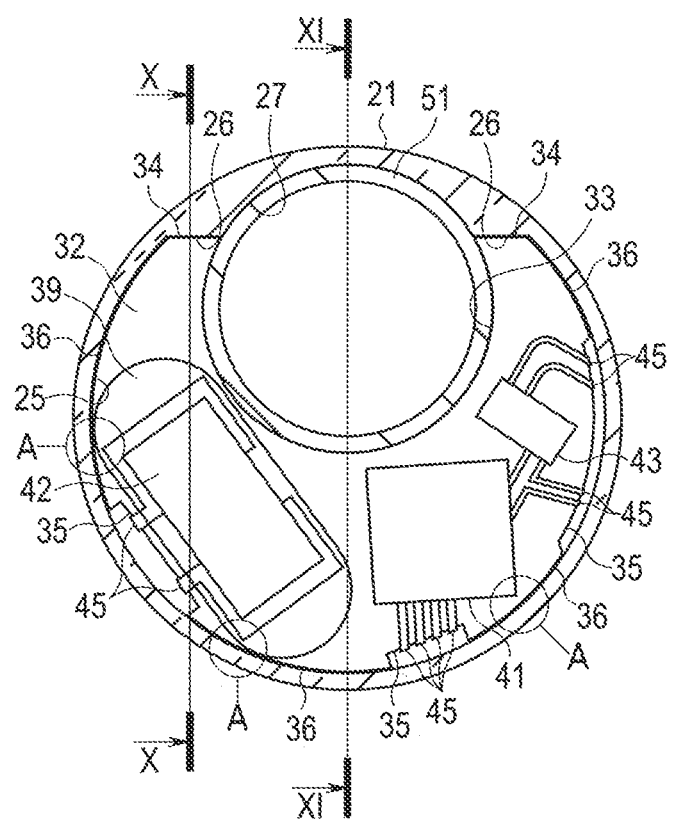
FIG. 9 is a cross-sectional view of the distal end portion of the endoscope according to the aspect of the present invention, which is taken along the line IX-IX in FIG. 8.
Figure 10:
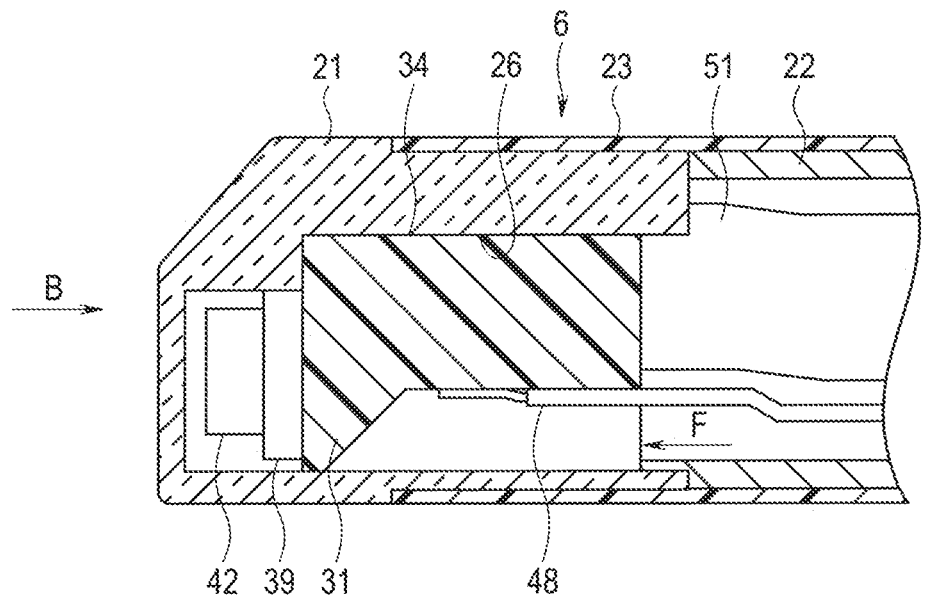
FIG. 10 is a cross-sectional view of the distal end portion of the endoscope according to the aspect of the present invention, which is taken along the line X-X in FIG. 9.
Figure 11:
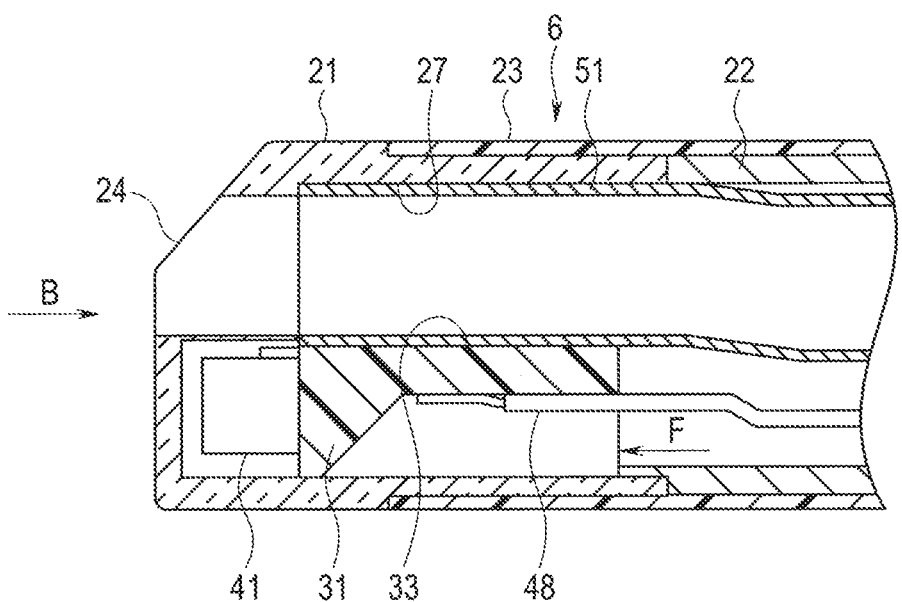
FIG. 11 is a cross-sectional view of the distal end portion of the endoscope according to the aspect of the present invention, which is taken along the line XI-XI in FIG. 9.
Figure 12:
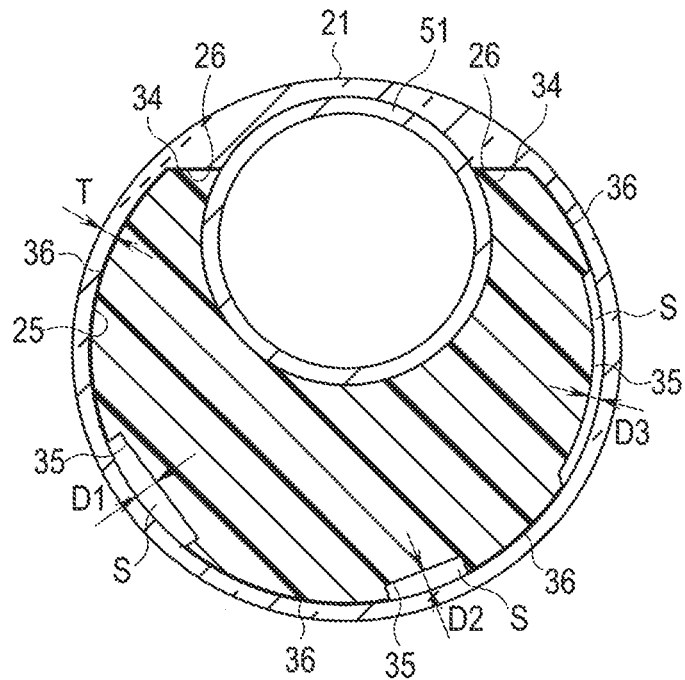
FIG. 12 is a schematic view of a cross section of the distal end portion of the endoscope according to the aspect of the present invention.
Figure 13:
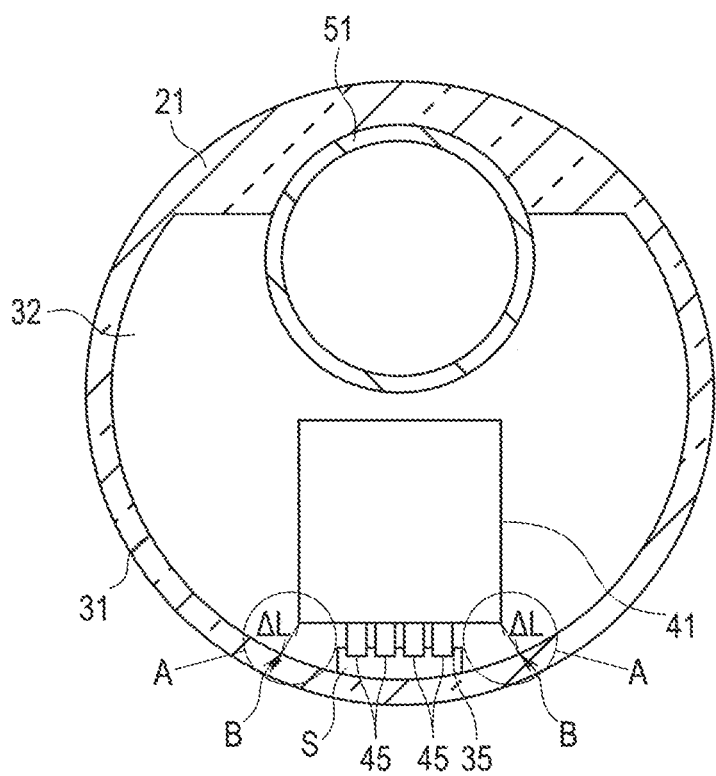
FIG. 13 is a schematic view of the cross section of the distal end portion of the endoscope according to the aspect of the present invention, and showing a first example of a state where a part at which the distal end cover and the distal end constituting portion are fitted to each other is provided in the vicinity of an electronic component.
Figure 14:
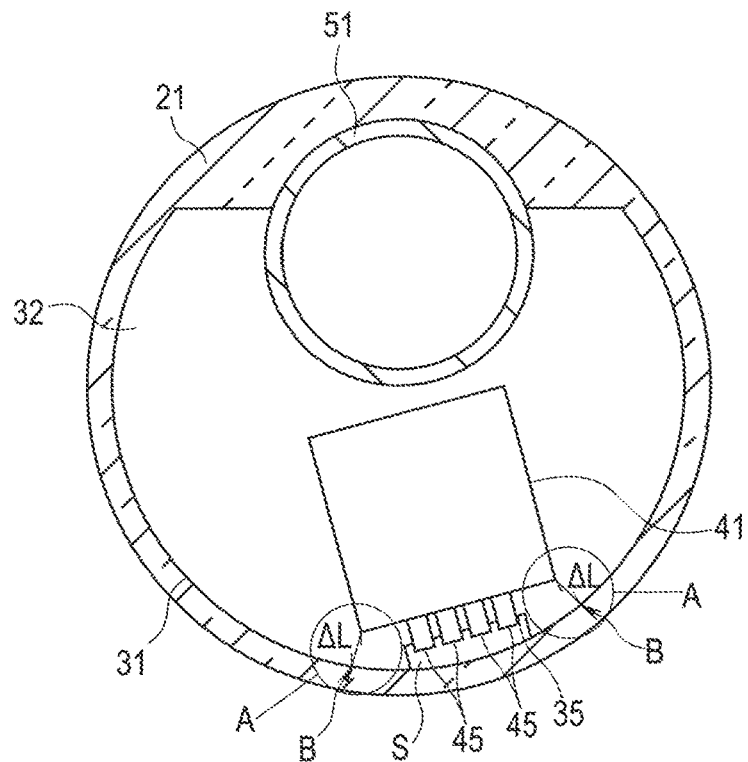
FIG. 14 is a schematic view of the cross section of the distal end portion of the endoscope according to the aspect of the present invention, and showing a second example of a state where the part at which the distal end cover and the distal end constituting portion are fitted to each other is provided in the vicinity of the electronic component.
Figure 15:
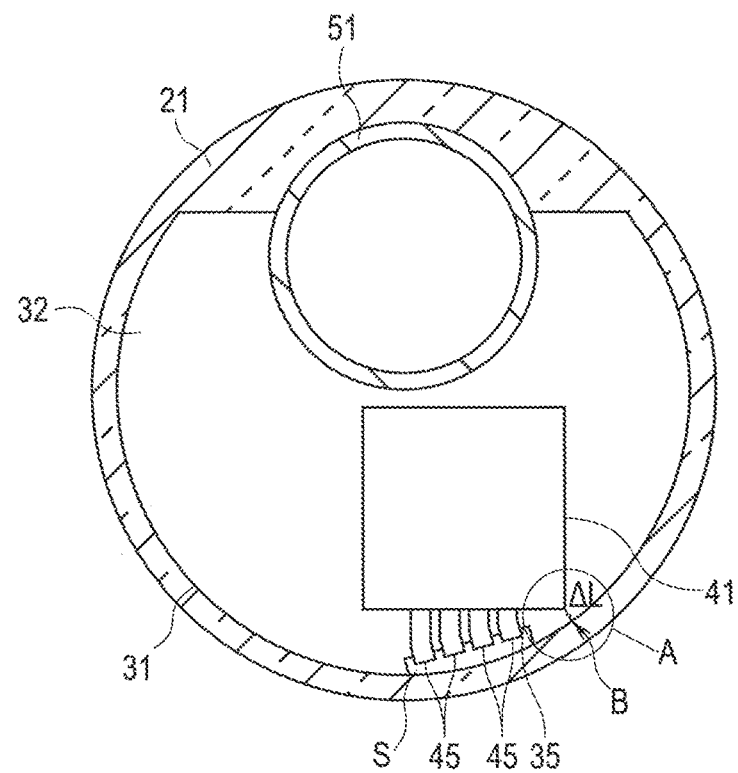
FIG. 15 is a schematic view of the cross section of the distal end portion of the endoscope according to the aspect of the present invention, and showing a third example of a state where the part at which the distal end cover and the distal end constituting portion are fitted to each other is provided in the vicinity of the electronic component.
Figure 16:
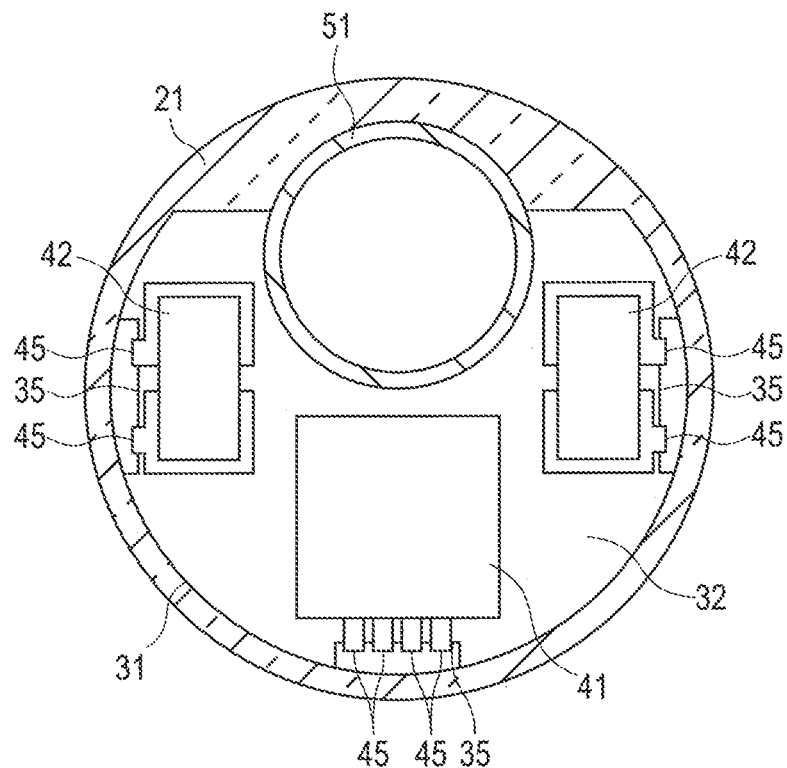
FIG. 16 relates to a modification of the distal end portion of the endoscope according to the aspect of the present invention, and is a cross-sectional view illustrating a configuration of a distal end portion.
Figure 17:
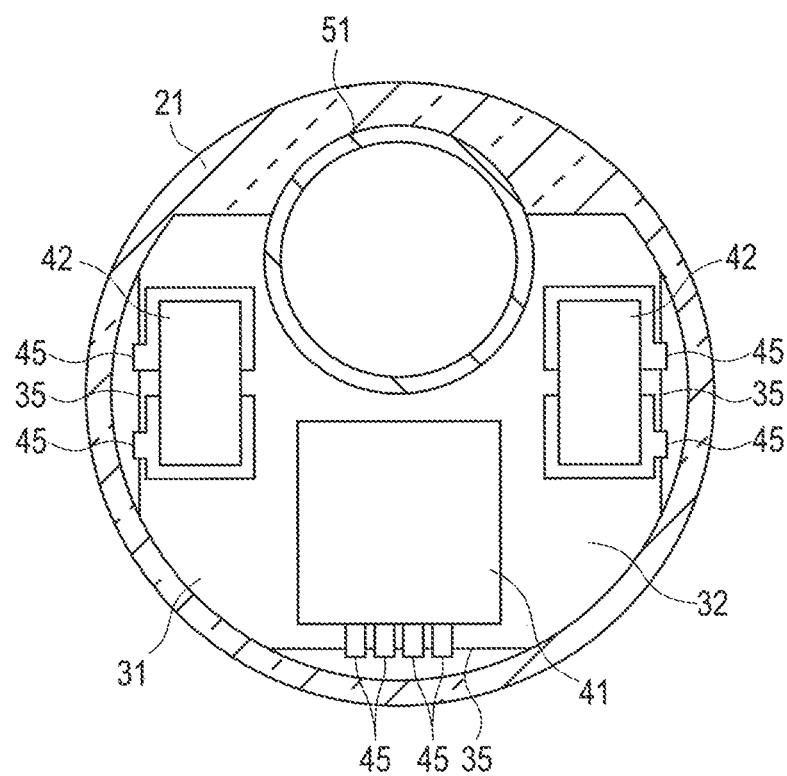
FIG. 17 relates to another modification of the distal end portion of the endoscope according to the aspect of the present invention, and is a cross-sectional view illustrating another configuration of a distal end portion, which is different from the configuration in the modification in FIG. 16.

FIG. 1 is a perspective view illustrating a configuration of the endoscope according to the one aspect of the present invention. FIG. 2 is a cross-sectional view illustrating a configuration of a distal end part of an insertion portion. FIG. 3 is a perspective view illustrating the configuration of the distal end part of the insertion portion. FIG. 4 is a perspective view illustrating a configuration of a distal end constituting portion. FIG. 5 is a front view illustrating the configuration of the distal end constituting portion. FIG. 6 is a plan view illustrating the configuration of the distal end constituting portion to which a plurality of cables are connected. FIG. 7 is an exploded perspective view illustrating a distal end cover and the distal end constituting portion. FIG. 8 is a side view illustrating the configuration of the distal end part of the insertion portion. FIG. 9 is a cross-sectional view of the distal end portion taken along the line IX-IX in FIG. 8. FIG. 10 is a cross-sectional view of the distal end portion taken along the line X-X in FIG. 9. FIG. 11 is a cross-sectional view of the distal end portion taken along the line XI-XI in FIG. 9. FIG. 12 is a schematic view illustrating a cross section of the distal end portion. FIG. 13 is a schematic view illustrating a cross section of the distal end portion, and showing a first example of a state where a part at which a distal end cover and the distal end constituting portion are fitted to each other is provided in the vicinity of an electronic component. FIG. 14 is a schematic view illustrating the cross section of the distal end portion, and showing a second example of a state where the part at which the distal end cover and the distal end constituting portion are fitted to each other is provided in the vicinity of the electronic component. FIG. 15 is a schematic view illustrating the cross section of the distal end portion, and showing a third example of a state where the part at which the distal end cover and the distal end constituting portion are fitted to each other is provided in the vicinity of the electronic component. FIG. 16 is a cross-sectional view illustrating a configuration of a distal end portion according to a modification. FIG. 17 is a cross-sectional view illustrating another configuration of a distal end portion according to another modification different from the modification in FIG. 16.

An endoscope 1 according to the present embodiment mainly includes an insertion portion 2, an operation portion 3, a universal cord 4, an electrical connector 5, and the like, as illustrated in FIG. 1. Although description will be made on the endoscope 1 according to the present embodiment by taking a ureteroscope as an example, the configuration of the essential part of the present invention provides a technology that is applicable to also various kinds of endoscopes including a bronchoscope, a flexible endoscope for digestive organs, and a surgical rigid endoscope, for example.

The insertion portion 2 is formed in an elongated shape and configured to be inserted into a subject. The insertion portion 2 is formed by including a distal end portion 6, a bending portion 7 as an endoscope bending portion, and a flexible tube portion 8 in this order from the distal end side. The insertion portion 2 has a pliability as a whole.

The distal end portion 6 of the insertion portion 2 incorporates inside thereof an image pickup unit, an illumination unit, and the like (none of them are illustrated here). The image pickup unit is an electronic component including inside thereof an image pickup device, etc. The illumination unit is an electronic component configured to emit illumination light forward.

The bending portion 7 is configured to actively bend in two directions along a first direction and a second direction opposite to the first direction, in response to rotation operation of a bending lever 13 for performing bending operation. The two directions are up and down directions in the present embodiment. The bending lever is one of the operation members provided at the operation portion 3. Note that the up and down directions referred to here indicate the up and down directions in an endoscopic image obtained by an image pickup with the image pickup unit.

In addition, the bending directions of the bending portion 7 are not limited to the two directions, i.e., the up and down directions. The bending portion 7 may be configured to actively bend in four directions, i.e., up, down, left, and right directions.

The flexible tube portion 8 is configured to have a pliability so as to be passively flexible. The flexible tube portion 8 includes inside thereof a channel for treatment instrument insertion. In addition, the flexible tube portion 8 includes inside thereof wirings such as various signal lines, electric cables, and the like.

Such wirings are electrically connected with the image pickup unit and the illumination unit that are incorporated in the distal end portion 6, passed through the inside of the operation portion 3, and extended from the inside of the universal cord 4 up to an electrical connector 5.

The operation portion 3 is provided continuously with the proximal end portion of the insertion portion 2. The operation portion 3 is a constituent unit including a plurality of operation members. The operation portion 3 includes a break-prevention portion 9, a grasping portion 10, a plurality of operation members (13, 14, etc.), a treatment instrument insertion portion 11, a suction valve 15, and the like.

The break-prevention portion 9 is provided at a connecting part that connects the distal end portion of the operation portion 3 and the proximal end portion of the flexible tube portion 8. The break-prevention portion 9 is a protection member configured to cover the proximal end portion of the flexible tube portion 8, to thereby prevent the flexible tube portion 8 from being broken unexpectedly and suddenly during the use of the endoscope 1.

The grasping portion 10 is a housing portion in which various constituent members are accommodated. The grasping portion 10 is connected with the break-prevention portion 9. The grasping portion 10 is a part to be held and grasped by the hand of the user at the time of using the endoscope 1.

The plurality of operation members are provided on the outer surface of the grasping portion 10 and configured to operate various functions of the endoscope 1. Examples of the plurality of operation members include the bending lever 13 for bending the bending portion 7 in the up and down directions, operation members for performing air/water feeding operation and suction operation, the operation member 14 for performing operations corresponding to operations of the image pickup unit and the illumination unit, etc.

The treatment instrument insertion portion 11 is a constituent portion including: a treatment instrument insertion port (not illustrated) through which various treatment instruments (not illustrated) are inserted; and a treatment instrument insertion path which is communicated with the treatment instrument insertion channel inside the operation portion 3.

Note that the treatment instrument insertion portion 11 includes a forceps plug 12 which is a lid member for opening and closing the treatment instrument insertion port and which is configured to be attachable to and detachable from (exchangeable with respect to) the treatment instrument insertion portion 11. In addition, the suction valve 15 is a coupling portion for coupling a suction conduit between the operation portion 3 and a suction device not illustrated.

The universal cord 4 is a hollow tubular member having flexibility and extended from the operation portion 3. The electrical connector 5 is a connecting member disposed at the distal end of the universal cord 4 and ensuring the connection between the endoscope and a video processor (not illustrated) as an external device, or the like.

As illustrated in FIG. 2, at the distal end part of the insertion portion 2, a cylindrical-shaped distal end cover 21 is disposed, a plurality of bending pieces 22 are incorporated, and a tubular bending rubber 23 is disposed. In the present embodiment, the distal end cover 21 is a transparent cover member disposed on the distal end portion 6. The plurality of bending pieces 22 are rotatably coupled with each other and provided in the bending portion 7. The bending rubber 23 is disposed from the halfway of the outer circumferential portion of the distal end cover 21 so as to integrally cover the plurality of bending pieces 22 as a bending tube.

As illustrated in FIG. 3, the distal end cover 21 incorporates inside thereof a distal end constituting portion 31 which is a member in the present embodiment and made of resin. Note that the distal end cover 21 includes, on the distal end surface thereof, an opening portion 24 through which the treatment instrument to be inserted into the insertion portion 2 is introduced and the treatment instrument inserted in the insertion portion 2 is led out.

Hereinafter, description will be made in detail on the configuration of the distal end constituting portion 31 according to the present embodiment.

As illustrated in FIG. 4, the distal end constituting portion 31 includes a plurality of electronic components mounted on a distal end surface 32. The plurality of electronic components include the image pickup unit 41 as an image pickup module, the illumination unit 42 as a light-emitting element, and a bypass capacitor 43, etc.

The illumination unit 42 is disposed on the distal end surface 32 of the distal end constituting portion 31 so as to be located on a placing surface higher than a placing surface on which the image pickup unit 41 is disposed. In other words, the distal end constituting portion 31 includes a protruding portion 39, which protrudes to the distal end side, on the part of the distal end surface at which the illumination unit 42 is mounted.

The protruding portion 39 forms a level difference on the distal end surface 32 of the distal end constituting portion 31, to thereby be capable of controlling the positions of the light-emission surface of the illumination unit 42 and the light-incident surface of the image pickup unit 41. As a result, the protruding portion 39 prevents unnecessary light (flare light, for example) from being incident on the image pickup unit 41.

The illumination unit 42 and the image pickup unit 41 may be disposed on the same placing surface on the distal end constituting portion 31. In such a case, at the time of mounting the respective electronic components, the supply of the bonding member (solder pastes, etc.) is stable, to thereby be capable of stably mounting the components.

Such a configuration can lead to an improvement in manufacturing yield. In addition, the configuration achieves simplification of the shape of the distal end constituting portion 31, which enables the distal end constituting portion 31 to be manufactured at a low cost.

In addition, the simplification of the shape of the distal end constituting portion 31 can reduce the space among the components, which results in the size reduction of the distal end constituting portion 31. As a result, the size of the distal end portion 6 of the insertion portion 2 can be reduced, thereby be capable of reducing the burden on a patient into which the insertion portion 2 is inserted.

The image pickup unit 41 includes a solid-state image pickup device such as CCD, CMOS or the like, which is an image sensor, a driving circuit, an objective lens, etc. The illumination unit 42 is a semiconductor device such as an LED.

The distal end constituting portion 31 includes a recess-shaped channel holding portion 33, the cross section of which has a circular shape, is formed in a direction of an axis connecting the distal end and the proximal end of the distal end constituting portion 31. The distal end constituting portion 31 is a substantially columnar-shaped block body including two plane portions 34 formed by partly cutting out the outer circumference of the part at which the channel holding portion is formed.

In addition, as illustrated in FIG. 5, a plurality of wiring placing surfaces 35 are formed on the side surface, which is the outer circumferential portion, of the distal end constituting portion 31. On the plurality of wiring placing surfaces 35, a plurality of wirings 45 are disposed. The plurality of wirings 45 are electrically connected with the electronic components such as the image pickup unit 41, the illumination unit 42 as the light-emitting element, and the bypass capacitor 43. The plurality of wiring placing surfaces 35 are bottom surfaces of groove portions each are formed in a recessed shape.

In other words, the plurality of wiring placing surfaces 35 configure a second side surface of the distal end constituting portion 31. The second side surface is formed in a stepped shape in the radially inward direction with respect to the outer circumferential surface 36 which is a first side surface of the distal end constituting portion 31.

The plurality of wiring placing surfaces 35 includes thereon the plurality of wirings 45 electrically connected with the electronic components such as the image pickup unit 41, the illumination unit 42 as the light-emitting element, and the bypass capacitor 43 that are mounted on the distal end surface 32 of the distal end constituting portion 31. The plurality of wirings 45 are formed as electrical conductor lines (circuits) to the proximal end side of the distal end constituting portion 31.

As illustrated in FIG. 6, the plurality of wirings 45 are formed up to a cable connecting portion 37 provided at the proximal end part of the distal end constituting portion 31, and are electrically connected with the plurality of terminals 38 of the cable connecting portion 37. The plurality of terminals 38 are connected with core wires of cables 48 such as various signal lines, electrical lines, etc., by solder or the like.

The distal end constituting portion 31 configured as described above is fitted to the distal end cover 21 by being inserted from the proximal end of the distal end cover 21, as illustrated in FIG. 7. Then, as illustrated in FIG. 8, the distal end cover 21 is connected with the distal-most one of the plurality of bending pieces 22, and the plurality of bending pieces 22 are covered with the bending rubber 23 from the halfway of the distal end cover 21. In addition, as illustrated in FIG. 9, a treatment instrument channel 51 formed in a tubular shape is disposed in the channel holding portion 33 of the distal end constituting portion 31.

In the present embodiment, the distal end cover 21 is transparent in order not to interfere with the incidence of the subject image into the image pickup unit 41 and emission of the illumination light from the illumination unit 42. However, the distal end cover 21 may be a non-transparent cover provided with an observation lens and an illumination lens.

Hereinafter, description will be made on a fitted state of the distal end constituting portion 31 to be disposed inside the distal end cover 21.

Firstly, as illustrated in FIGS. 9 and 10, the distal end cover 21 includes an inner circumferential surface 25. The inner circumferential surface 25 is the inner surface of a hole portion into which the distal end constituting portion 31 is inserted. The inner circumferential surface 25 is configured to come into surface contact with the outer circumferential surface 36 of the distal end constituting portion 31.

Note that the electronic components such as the image pickup unit 41, the illumination unit 42, etc., that are mounted on the distal end constituting portion 31 are preferably located in the vicinity of the parts at which the distal end constituting portion 31 is fitted to the distal end cover 21 by the outer circumferential surface 36 of the distal end constituting portion coming into surface contact with the inner circumferential surface 25 of the distal end cover (see the circles A in FIG. 9).

The electronic components such as the image pickup unit 41, the illumination unit 42, etc., are thus disposed, to thereby enable an efficient mounting of the components in a narrow region and achieve the reduction in the diameter of the distal end portion.

In addition, the distal end cover 21 is formed to be partially thick in the radially inward direction, and includes two holding surfaces 26 that are configured to come into surface contact respectively with the two plane portions 34 formed by cutting out the vicinity of the channel holding portion 33 in which the treatment instrument channel 51 of the distal end constituting portion 31 is disposed.

Therefore, the distal end constituting portion 31 has a structure in which the distal end constituting portion 31 cannot be fitted to the inside of the distal end cover 21 unless the distal end constituting portion 31 is inserted into the distal end cover 21 such that the outer circumferential surface 36 and the two plane portions 34 come into surface contact respectively with the inner circumferential surface 25 and the two holding surfaces 26. In other words, the surface-contact of the plurality of surfaces provide a positioning structure at the time of fitting the distal end constituting portion 31 to the distal end cover 21.

Note that the distal end cover 21 includes an arc surface 27 formed between the two holding surfaces 26. The arc surface 27 is configured to come into surface contact with a part of the outer circumference of the treatment instrument channel 51, as illustrated in FIGS. 9 and 11. With such a configuration, the treatment instrument channel 51 is adhered and fixed, with the outer circumferential portion thereof being covered and held by the channel holding portion 33 of the distal end constituting portion 31 and the arc surface 27 which is a holding portion on the side of the distal end cover 21.

Furthermore, the distal-most one of the bending pieces 22 is connected to the proximal end part of the distal end cover 21, thereby providing a structure in which the front and back end surfaces of the distal end constituting portion 31 fitted in the distal end cover 21 are sandwiched between the distal end cover 21 and the distal-most one of the bending pieces 22.

In other words, the distal end constituting portion 31 in the distal end cover 21 is fixed in the state where a part of the distal end surface is in contact with the distal end cover 21 and a part of the proximal end surface is in contact with the distal-most one of the bending pieces 22 to be sandwiched between the distal end cover and the distal-most one of the bending pieces (in the state where the distal end constituting portion 31 receives the forces illustrated by the arrows F and B in FIGS. 10 and 11). Note that the distal end constituting portion 31 may be firmly fixed by filling inside the distal end cover 21 with adhesive.

In the state where the distal end constituting portion 31 is fitted in the distal end cover 21, the distal end constituting portion 31 has gaps formed by the plurality of wiring placing surfaces 35 on which the plurality of wirings 45 are disposed being separated by a predetermined distance from the inner circumferential surface 25 of the distal end cover 21 in the radially inward direction. The plurality of wirings 45 are disposed respectively in the gaps.

In other words, as illustrated in FIG. 12, a plurality of spaces S are formed such that the plurality of wiring placing surfaces 35 of the distal end constituting portion 31 have predetermined depths D1, D2, and D3 in the radially inward direction with respect to the inner circumferential surface 25 of the distal end cover 21. The plurality of wirings 45 are disposed respectively in the plurality of spaces S.

Accommodating the plurality of wirings 45 respectively in the plurality of spaces S provides a structure that prevents the plurality of wirings 45 from protruding in the radially outward direction with respect to the outer circumferential surface 36 of the distal end constituting portion 31. Such a structure enables the distal end cover 21 to have a minimum thickness T having a predetermined rigidity, without increasing the thickness of the distal end cover 21 more than necessary. As a result, the diameter of the distal end portion 6 of the insertion portion 2 of the endoscope 1 can be reduced, which can lead to an improvement in the insertion performance of the insertion portion 2 into the lumen of the subject.

Furthermore, as illustrated in FIGS. 13 to 15, the distal end cover 21 and the distal end constituting portion 31 are fitted to each other in the radial direction at the part where the distance ΔL between the outer circumference of the distal end constituting portion 31 and the electronic components such as the image pickup unit 41 (the illumination unit 42 are not illustrated in the above-mentioned drawings) mounted on the distal end surface 32 of the distal end constituting portion 31 is the shortest (the parts illustrated by the arrows B in the circles A).

Such a configuration enables the electronic components such as the image pickup unit 41 (illumination unit 42) to be mounted efficiently in the narrow region, to thereby be capable of reducing the outer diameter of the distal end constituting portion 31. As a result, reduction in the diameter of the distal end portion can be achieved.

Note that the distal end constituting portion 31 may be formed by a molded interconnect device (MID) and the plurality of wirings 45 of the metal film may be formed respectively on the plurality of wiring placing surfaces 35 or the plurality of wirings 45 may be disposed on the plurality of wiring placing surfaces 35 so as to be accommodated in the plurality of spaces S formed in the radially inward direction with respect to the inner circumferential surface 25 of the distal end cover 21.

The distal end constituting portion 31 may be formed by using a substrate such as a glass epoxy substrate, a ceramic substrate, a silicon substrate, a glass substrate, or a flexible printed substrate, instead of the molded interconnect device (MID).

Modifications

The distal end constituting portion 31 may be configured such that the plurality of wiring placing surfaces 35 in which the plurality of wirings 45 are disposed are formed as recess-shaped groove portions as illustrated in FIG. 16, similarly as in the configuration recited in the above-described embodiment. Alternatively, as illustrated in FIG. 17, the plurality of wiring placing surfaces 35 in which the plurality of wirings 45 are disposed may be formed by partly cutting out the outer circumference of the distal end constituting portion 31 in a plane shape. Note that each of FIGS. 16 and 17 illustrates an example in which two illumination units 42 are provided.

The electronic components mounted on the distal end constituting portion 31 in the above described embodiment and the modifications are not limited to the image pickup system and the illumination system, but include the electronic components incorporated in the distal end portion 6 of the endoscope 1.

Furthermore, the endoscope 1 may be configured to transmit illumination light with a light guide, instead of using the illumination unit 42 as the electronic component.

The present invention is not limited to the above-described embodiment, but various modifications are possible without departing from the gist of the present invention.

What is claimed is:

1. A distal end portion for use with an endoscope, the distal end portion comprising:
    a distal end cover configured to be disposed at a distal end of the endoscope, the distal end cover having an inner surface;
    a plurality of electronic components;
    a plurality of wires electrically connected to the plurality of electronic components; and
    a distal end member located in the distal end cover, the distal end member comprising a first side surface, a plurality of second side surfaces, and a distal end surface;
    wherein the plurality of electronic components are directly mounted on the distal end surface,
    the first side surface and each of the plurality of second side surfaces directly extend from the distal end surface along a longitudinal direction of the distal end member,
    the first side surface is in contact with the inner surface,
    each of the plurality of second side surfaces are offset in a radially inward direction relative to the first side surface,
    each of the plurality of second side surfaces and a corresponding portion of the inner surface define a separate non-contiguous space;
    a portion of the plurality of wires is disposed in each space,
    the distal end member includes a plane surface, and
    the distal end cover includes a holding surface configured to come into surface contact with the plane surface and to define and position an inserting and fitting position of the distal end member.

2. The distal end portion according to claim 1, wherein the plurality of electronic components are directly mounted on the distal end surface so as to be located adjacent to where the inner surface and the first side surface come into surface contact with each other.

3. The distal end portion according to claim 1, wherein the distal end member includes a partial treatment instrument surface; and
    the inner surface of the distal end cover and the partial treatment instrument channel surface collectively define a treatment instrument channel.

4. The endoscope according to claim 1, wherein an electronic component of the plurality of electronic components has an outer rectangular shape when viewed in a direction towards the distal end surface, a first side of the rectangle is a side closest to a corresponding second surface of the plurality of second side surfaces.

5. The endoscope according to claim 4, wherein the portion of the plurality of wires extend from the first side of the rectangle toward a proximal end of the distal end portion through the space.

6. The distal end portion according to claim 4, wherein a distance between a corner portion formed at an end of the first side of the rectangle and an outer circumference of the distal end member is shorter than a distance between other portions of the rectangle and the outer circumference of the distal end member.

7. The distal end portion according to claim 4, wherein a width of the closest side surface of the plurality of second side surfaces in a circumferential direction is shorter than the first side of the rectangle.

8. The distal end portion according to claim 4, wherein a width of the closest side surface of the plurality of second side surfaces in a circumferential direction is longer than the first side of the rectangle.

9. The distal end portion of the endoscope according to claim 1, wherein:
the distal end member further includes a recess,
the distal end portion further comprises a channel defined by the inner surface and the recess.

10. The distal end portion of the endoscope according to claim 9, further comprising a channel tube located in the channel.

11. An endoscope comprising:
a distal end portion, the distal end portion comprising:
a distal end cover configured to be disposed at a distal end of the endoscope, the distal end cover having an inner surface;
a plurality of electronic components;
a plurality of wires electrically connected to the plurality of electronic components; and
a distal end member located in the distal end cover, the distal end member comprising a first side surface, a plurality of second side surfaces surface, and a distal end surface;
wherein the plurality of electronic components are directly mounted on the distal end surface,
the first side surface and each of the plurality of second side surfaces directly extend from the distal end surface along a longitudinal direction of the distal end member,
the first side surface being is in contact with the inner surface,
each of the plurality of second side surfaces are offset in a radially inward direction relative to the first side surface,
each of the plurality of second side surfaces and a corresponding portion of the inner surface define a separate non-contiguous space,
a portion of the plurality of wires is disposed in each space,
the distal end member further includes a recess,
the distal end portion further comprises a channel defined by the inner surface and the recess.

12. The endoscope according to claim 11, wherein
the insertion portion includes a bending portion including a bending tube is connected to a proximal end of the distal end cover, and
the distal end member is brought into contact with each of the distal end cover and the bending tube and fixed by being sandwiched between the distal end cover and the bending tube.

13. The endoscope according to claim 11, wherein an electronic component of the plurality of electronic components has an outer rectangular shape when viewed in a direction towards the distal end surface, a first side of the rectangle is a side closest to a corresponding second surface of the plurality of second side surfaces.

14. The endoscope according to claim 13, wherein the portion of the plurality of wires extend from the first side of the rectangle toward a proximal end of the distal end portion through the space.

15. The endoscope according to claim 13, wherein a width of the closest side surface of the plurality of second side surfaces in a circumferential direction is shorter than the first side of the rectangle.

16. The endoscope according to claim 13, wherein a width of the closest side surface of the plurality of second side surfaces in a circumferential direction is longer than the first side of the rectangle.

17. The endoscope according to claim 11, wherein the distal end portion further comprises a channel tube located in the channel.

18. An endoscope comprising:
a distal end portion, the distal end portion comprising:
a distal end cover disposed at a distal end of an insertion portion;
a distal end member configured to be inserted into and fitted to the distal end cover, the distal end member comprising a first side surface and a second side surface, the first side surface being configured to come into surface contact with an inner surface of the distal end cover, the second side surface being formed in a radially inward direction with respect to the first side surface, the second side surface forming a space by being separated from the inner surface of the distal end cover by a predetermined distance;
an electronic component mounted on a distal end surface of the distal end member, the electronic component having an outer shape formed in rectangle and being disposed such that one side of the rectangle is along the second side surface; and
a wiring electrically connected to the electronic component from a side of the one side of the rectangle, the wiring being disposed in the space formed between the inner surface of the distal end cover and the second side surface of the distal end member;
wherein the distal end member and the distal end cover respectively have holding portions configured to fix a treatment instrument channel by covering and holding an outer circumferential portion of the treatment instrument channel.

* * * * *